United States Patent [19]

Schnettler et al.

[11] Patent Number: 4,728,661
[45] Date of Patent: Mar. 1, 1988

[54] CARDIOTONIC PHENYL OXAZOLONES

[75] Inventors: Richard A. Schnettler; Winton D. Jones, Jr.; George P. Claxton, all of Cincinnati, Ohio

[73] Assignee: Merrell Dow Pharmaceuticals Inc., Cincinnati, Ohio

[21] Appl. No.: 797,578

[22] Filed: Nov. 13, 1985

[51] Int. Cl.$^4$ .............................................. A61K 31/42
[52] U.S. Cl. ..................................................... 514/376
[58] Field of Search ......................................... 514/376

[56] References Cited

U.S. PATENT DOCUMENTS

| | | | |
|---|---|---|---|
| 3,897,410 | 4/1975 | Bottari et al. | 524/792 |
| 4,188,323 | 2/1980 | Pestellini et al. | 548/229 |
| 4,532,250 | 7/1985 | Stout et al. | 514/341 |

FOREIGN PATENT DOCUMENTS

| | | | |
|---|---|---|---|
| 2205676 | 8/1972 | Fed. Rep. of Germany | 514/376 |
| 2351948 | 4/1974 | Fed. Rep. of Germany | |
| 2935902 | 4/1981 | Fed. Rep. of Germany | |
| 2156486 | 6/1973 | France | |
| 7654553 | 11/1974 | Japan | |
| 7611763 | 1/1976 | Japan | |
| 1305273 | 1/1973 | United Kingdom | |
| 427015 | 12/1974 | U.S.S.R. | |

OTHER PUBLICATIONS

Chem. Abst. 79:126485m (1973)—Derible et al.
Chemical Abstracts 101:6947q abstracting W. Blommerde, et al., J. Org. Chem. 49(12), 2231–2235 (1984).
Chemical Abstracts 86:29695s, abstracting B. Kreig and P. Konieczny, Justus Liebigs Ann. Chem., 10, 1862–1872 (1976).
Chemical Abstracts 76:140606w, abstracting E. D. Sych, et al, Khim Geterotsikl. Soedin., 282–285 (1970).
Nakagawa M., et al., Agric. Biol. Chem. 38(11):2205-8 (1974).
Nakagawa M. et al., Agric. Biol. Chem. 39(9):1763-73 (1975).
Fukumi H. et al., Heterocycles 12(10):1297-9 (1979).
Shvaika O. P., Klimisha GP. Dopov. Akad. Nauk Ukr. RSR, Ser. B 32(4):350-2 (1970).
Bottari F, et al., J. Med. Chem. 15(1):39–42 (1972).
Roderhorst RM, Koch TH. J. Am. Chem. Soc. 97(25):7298–304 (1975).
Saettorne MF, et al., Gazz. Chim. Ital. 96(11):1615–29 (1966).
Krieg B., Konieczny P. Justsus Liebigs Ann. Chem. (10:1862–72 (1976).
Dziomko VA, Ivashchenko AV, ZH. Org. Khim. 9(10):2191–4 (1973).
Chem. Abst. 100:103228(t) (1984)—Shvaika et al.
Chem. Abst. 101:38519(t) (1984)—Yamamoto et al.
Chem. Abst. 80:27154(s) (1974)—Dziomko et al.

*Primary Examiner*—Douglas W. Robinson
*Attorney, Agent, or Firm*—Stephen L. Nesbitt

[57] ABSTRACT

Phenyloxazolones are useful as cardiotonics in the treatment of heart failure and enhance cardiac function.

14 Claims, No Drawings

CARDIOTONIC PHENYL OXAZOLONES

BACKGROUND OF THE INVENTION

This invention relates to the use of certain phenyl oxazolones as cardiotonics in the treatment of heart failure.

Heart failure is that physiological condition resulting from the inability of the ventricular myocardium to maintain adequate blood flow to the peripheral body tissues and includes congestive heart failure, backward and forward heart failure, right ventricular and left ventricular heart failure, and low-output heart failure. Heart failure can be caused by myocardial ischemia, myocardial infarction, excessive alcohol usage, pulmonary embolism, infection, anemia, arrhythmias, and systemic hypertension. Symptoms include tachycardia, fatigue with exertion, dyspnea, orthopnea and pulmonary edema.

Treatment involves either removal or correction of the underlying cause or involves control of the heart failure state. Management or control can be accomplished by increasing cardiac output or by decreasing cardiac work load. While work load can be reduced by reduction of physical activities and physical and emotional rest, increasing cardiac output has traditionally involved therapy with digitalis or a digitalis glycoside and more recently vasodilator therapy. Digitalis stimulates contractile force of the heart which increases cardiac output and improves ventricular emptying. In this way, digitalis therapy normalizes venous pressure and reduces peripheral vasoconstriction, circulatory congestion and organ hypoperfusion.

Unfortunately, optimal doses of digitalis vary with the patient's age, size and condition and the therapeutic to toxic ratio is quite narrow. In most patients the lethal dose is only above five to ten times the minimal effective dose with toxic effects becoming apparent at only 1.5 to 2.0 times the effective dose. For these reasons, dose must be carefully tailored to suit the individual and frequent clinical examination and electrocardiogram are necessary to detect early signs of digitalis intoxication. Despite this care digitalis intoxication is reported in up to one-fifth of hospitalized patients undergoing therapy.

Vasodilator therapy increases cardiac output and improved ventricular emptying by reducing the systemic blood pressure against which the heart must pump. However, in severe heart failure a vasodilator alone may not improve cardiac function sufficiently due to the weakness of the myocardial contractility necessitating the concomitant use of digitalis. Moreover a rapid tolerance has been reported to develop to the effects of vasodilator therapy in heart failure patients. The need for less toxic and more effective cardiotonic agents is readily apparent. Applicants have discovered certain phenyl oxazolones which possess potent cardiotonic activity and by comparison to digitalis have few toxic effects.

SUMMARY OF THE INVENTION

This invention is directed to the use of phenyl oxazolones of formula 1

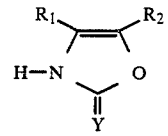

wherein Y is an oxygen or sulfur group;

and $R_1$ and $R_2$ are each independently selected from a hydrogen, a $(C_1-C_5)$alkyl group, or a phenyl group optionally substituted with one or two members of the group consisting of $(C_1-C_5)$alkyl, $(C_1-C_5)$alkoxy, $(C_1-C_5)$alkylthio, $(C_1-C_5)$alkylsulfinyl, $(C_1-C_5)$alkylsulfonyl, hydroxy, halogen, cyano, carboxy, carb($C_1-C_5$)alkoxy, carbamido, $(C_1-C_5)$alkanoylamino, imidazolyl, or trifluoromethyl or with a methylenedioxy group; with the proviso that one of $R_1$ and $R_2$ but not both of $R_1$ and $R_2$ must be a hydrogen or a $(C_1-C_5)$alkyl.

DETAILED DESCRIPTION OF THE INVENTION

The formula 1 compounds exist in several tautomeric. Throughout this disclosure, phenyl oxazolones of formula 1 are intended to include these tautomers as well.

The ring nitrogen of the formula 1 compounds can be substituted with a $(C_1-C_5)$alkyl group, an alkanoyl group such as an acetyl group, or a benzoyl group. These nitrogen substituted compounds are equivalent to the unsubstituted compounds primarily because the substituent is cleaned upon administration to a patient but also because many of the nitrogen substituted compounds independently possess significant ability to enhance myocardial contractile force and are useful cardiotonic agents.

As used herein the term $(C_1-C_5)$alkyl and the alkyl portion of the alkoxy, alkylthio, alkylsulfinyl, alkylsulfonyl, carbalkoxy and carbamidoalkanoyl groups means a straight or branched alkyl group of from one to five carbon atoms. Illustrative examples of a $C_1$-alkyl group are methyl, ethyl, isopropyl, butyl, sec-butyl and pentyl. The term halogen means a fluoro, chloro, bromo or iodo group. Imidazolyl includes 1-, 2-, 3-, 4- and 5 imidazolyl.

As is true for most classes of therapeutically effective compounds, certain subclasses are more effective than others. In this instance those compounds of formula 1 wherein Y is an oxo group are preferred. Also preferred are those compounds wherein $R_1$ is a $(C_1-C_5)$alkyl group or wherein $R_2$ is a $(C_1-C_5)$alkyl group. More preferred are those compounds of formula 1 where $R_1$ is a $(C_1-C_5)$alkyl group and $R_2$ is an optionally substituted phenyl. The most preferred compounds of formula 1 are those wherein $R_1$ is a methyl, ethyl or propyl group and wherein $R_2$ is a substituted phenyl group.

The compounds of formula 1 can be prepared by standard techniques analogously known in the art. In fact many of the formula 1 compounds are reported in the chemical literature. For example those compounds of formula 1 wherein $R_2$ is a hydrogen group can be prepared by the procedures described in U.S. Pat. No. 3,879,410.

In another general procedure a bromoketone of formula 2A or 2B

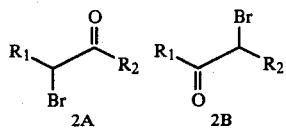

wherein $R_1$ and $R_2$ are as defined above is allowed to react with a cyanate or thiocyanate salt preferably sodium or potassium cyanate or thiocyanate to form the corresponding isocyanate or isothiocyanate of formula 3A or 3B

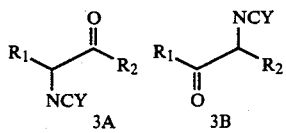

wherein Y, $R_1$ or $R_2$ are as defined above. This reaction can be performed by mixing the bromoketone with from about 1 to 5 molar equivalents of the cyanate or thiocyanate salt in a suitable solvent. The reaction is allowed to proceed for about 5 minutes to about 10 hours depending on the reactants, the solvent and the temperature which can be from about 0° to 100° C., preferably about 80° C. A suitable solvent is any nonreactive solvent such as water or water miscible solvent for example an organic acid such as acetic acid, an alcohol such as methanol or ethanol or an ether such as tetrahydrofuran or p-dioxan. Preferably any nonaqueous solvent is mixed with water. The preferred solvent is water. The product can be isolated and purified by any suitable procedure. The resulting compound of formula 4 when heated, typically as a melt at from 90° to 110° C., without solvent, cyclizes to form a compound of formula 1.

Another procedure involves allowing a hydroxyketone of structure 4A or 4B.

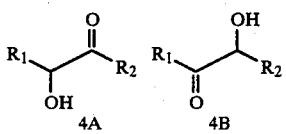

wherein $R_1$ and $R_2$ are as defined above to react with a cyanate or thiocyanate salt in the presence of an acid. Here again the cyanate or thiocyanate salt is typically sodium or potassium cyanate or thiocyanate. The acid can be any suitable acid such as hydrochloric acid. This reaction is normally performed in aqueous solution but any other organic solvent may be used. The reactants are mixed typically with a molar excess of the cyanate or thiocyanate salt and allowed to react for from 10 minutes to about a day at from 0° to 100° C., preferably from 25° to 80° C. The product is isolated and purified by conventional means such as by solvent removal and chromatography followed by recrystallization, typically from ethanol.

The bromo-ketones of formula 2A and 2B are either known in the art or can be readily prepared by standard techniques. For example the des-bromo analog of a structure 2A or 2B compound can be treated with bromine. Where the group adjacent to the carbon to be brominated is a hydrogen or a $(C_1-C_5)$alkyl group, a radical initiator can be used to promote the bromination. Suitable initiators include iron metal and N-bromosuccinimide. The bromination can also be accomplished by addition of concentrated hydrobromic acid, typically 48% aqueous hydrobromic acid, to a solution containing the des-bromo compound.

The structure 4A or 4B hydroxy-ketones can also be readily prepared in any suitable manner. For example a structure 2A or 2B bromo-ketone can be allowed to react with an acetate salt, preferably potassium acetate, to form the corresponding acetyloxy-ketone which upon treatment with an acid, such as hydrochloric acid, yields the desired structure 4A or 4B compound. This nucleophilic substitution reaction is performed by mixing the reactant preferably with an excess of acetate salt, and allowing the reaction to proceed from 10 minutes to 1 day, typically from 1 to 6 hours, depending on the reactants, the solvents, and the temperature which can be from 0° to 120° C., preferably from 25° to 80° C. Suitable solvents are any nonreactive solvent but those organic solvents which promote nucleophilic reactions are preferred including dimethylformamide, dimethylsulfoxide, diethyl ether, tetrahydrofuran and p-dioxan. Acetonitrile is the most preferred solvent. This reaction may be promoted by the presence of a chelating agent to trap the cation of the acetate salt. The Crown ethers are particularly effective. When potassium acetate is the acetate salt utilized, the crown ether known as 18-crown-6 is especially effective.

The structure 4A and 4B hydroxyketones can also be prepared by the acid catalyzed saponification of a compound of structure 5A or 5B

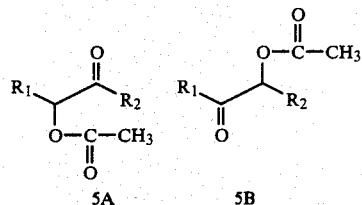

wherein $R_1$ and $R_2$ are as defined above. In many of the saponifications performed by the applicants, a concurrent transposition of the hydroxy and keto functionalities occurred. Thus many of the structure 5A compounds when saponified result in a hydroxy-ketone of structure 4B and many of the structure 5B compounds result in a structure 4A hydroxy-ketone. Presently applicants are unable to predict with certainty whether the transposition will occur because apparently subtle differences in the reactants are determinative. For example the structure 5A compound wherein $R_1$ is an ethyl group and $R_2$ is a 4-pyridyl group which saponified results in the transposed structure 4B compound while the closely analogous structure 5A compound wherein $R_1$ is an ethyl group and $R_2$ is a 2-pyridyl group results in the nontransposed structure 4A compound. Many such saponifications result in mixtures of transposed and nontransposed products. While accurate predictions are not possible the ordinary artisan can readily ascertain whether the desired 4A or 4B compound results and if not the desired compound can be prepared by an alternate procedure.

The compounds of formula 1 are cadiotonic agents useful in the treatment of heart failure. The utility of formula 1 compounds as cardiotonics and their ability to enhance cardiac function may be determined by administering the test compound (0.1-100 mg/kg) intravenously, intraperitoneally, intraduodenally or intragastrically in a suitable vehicle to a mongrel dog (either sex). The test dogs are anesthetized and prepared by isolating a suitable artery (e.g., femoral or common carotid) and vein (e.g., femoral or external jugular) and introducing polyethylene catheters filled with 0.1% Heparin-Na to record arterial blood pressure and administer compounds, respectively. The chest is opened by splitting the sternum at the midline or by an incision at the left fifth intercostal space, and a pericardial cradle is formed to support the heart. A Walton-Brodie strain gage is sutured to the right or left ventricle to monitor myocardial contractile force. An electromagnetic flow probe may be placed around the root of the ascending aorta for measuring cardiac output less coronary blood flow. A catheter may also be put into the left atrium or the left ventricle of the heart to record left atrial pressure or left ventricular pressure. Heart failure is induced by administering sodium pentobarbital (20 to 40 mg/kg) followed by a continuous infusion of 0.25–2 mg/kg/min. or propranalol hydrochloride (4 mg/kg) followed by a continuous infusion of 0.18 mg/kg/min. to the blood perfusing the heart. Following administration of either of these cardiac depressants, the right atrial pressure dramatically increases and cardiac output is severly depressed. Reversal of these effects by the test compound indicates cardiotonic activity.

The compounds may be administered in various manners to achieve the desired effect. The compounds may be administered alone or in the form of pharmaceutical preparations to the patient being treated either topically, orally or parenterally, that is, intravenously or intramuscularly. The amount of compound administered will vary with the patient, the severity of the cardiac failure and the mode of administration.

For topical, oral or parenteral administration the cardiotonically effective amount of compound and the amount required to enhance myocardial contractile force is from about 0.1 mg/kg of patients body weight per day up to about 400 mg/kg of patient body weight per day and preferably from about 0.3 mg/kg of patient body weight per day up to about 120 mg/kg of patient body weight per day.

For oral administration a unit dosage may contain, for example, from 5 to 700 mg of the active ingredient, preferably about 15 to 500 mg of the active ingredient. For parenteral administration a unit dosage may contain, for example, from 5 to 700 mg of the ctive ingredient, preferably about 15 to 210 mg. Repetitive daily administration of the compounds may be desired and will vary with the condition of the patient and the mode of administration.

As used herein, the term "patient" is taken to mean warm blooded animals, for example, birds, such as chickens and turkeys, and mammals, such as sheep, horses, bovine cows and bulls, pigs, dogs, cats, rats, mice and primates, including humans.

For oral administration the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose and cornstarch. In another embodiment the compounds of general formula 1 can be tableted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compounds in a physiologically acceptable diluent with a pharmaceutical carrier which can be a sterile liquid such as water, alcohols, oils and other acceptable organic solvents with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanol and glycols such as propylene glycol or polyethylene glycol or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, a silicone rubber manufactured by the Dow-Corning Corporation.

The following specific examples further illustrate the preparation and use of the compounds of formula 1 but are not intended to limit the scope of the invention.

EXAMPLE 1

4-Ethyl-5-[4-(1-Imidazolyl)phenyl]-2(3H)-Oxazolone

1′-Imida 20yl-2-Aminobutyrophenone dihydrochloride (3.2 g, 0.01 ml) was dissolved in water (40 ml) at 0° C. and treated with N,N′-Carbonyldiimidazole (5.2 g) with vigorous stirring. The resulting imidazoylacyl amide was extracted with ethylacetate. The extract was dried and evaporated to dryness. The residue was heated under vacuum. Imidazole was eliminated leaving an isocyanate which upon further heating gave the desired oxazolone, mp 263°–66° C. (dec.)

EXAMPLE 2

| A tablet is prepared from | |
|---|---|
| 4-methyl-5-phenyl-2(3H)—oxazolone | 250 mg |
| starch | 40 mg |
| talc | 10 mg |
| magnesium stearate | 10 mg |

EXAMPLE 3

| A capsule is prepared from | |
|---|---|
| 4-ethyl-5-(4-methoxyphenyl)-2(3H)—oxazolone | 400 mg |
| talc | 40 mg |
| sodium carboxymethylcellulose | 40 mg |
| starch | 120 mg |

We claim:

1. A method of treating heart failure in a patient in need thereof which comprises administering to the patient a cardiotonically effective amount of a phenyl oxazolone of the formula

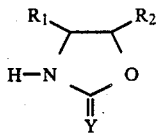

wherein Y is an oxygen or sulfur group; and
  $R_1$ is a hydrogen, or a $(C_1-C_5)$alkyl group, $R_2$ is a phenyl group optionally substituted with one or two members of the group consisting of $(C_1-C_5)$alkyl, $(C_1-C_5)$alkoxy,
  $(C_1-C_5)$alkylthio, $(C_1-C_5)$alkylsulfinyl,
  $(C_1-C_5)$alkylsulfonyl, hydroxy, halogen,
  cyano, carboxy, carb$(C_1-C_5)$alkoxy,
  carbamido, $(C_1-C_5)$alkanoylamino,
  imidazolyl, trifluoromethyl or with a methylenedioxy group.

2. A method of claim 1 wherein Y is an oxygen group.

3. A method of claim 2 wherein $R_1$ is a $(C_1-C_5)$alkyl group.

4. A method of claim 2 wherein $R_2$ is an unsubstituted phenyl group.

5. A method of claim 3 wherein $R_2$ is a substituted phenyl group.

6. A method of claim 2 wherein $R_1$ is a methyl, ethyl or propyl group.

7. A method of claim 6 wherein $R_2$ is a substituted phenyl group.

8. A method of enhancing myocardial contractile function in a patient in need thereof which comprises administering to the patient an effective amount of phenyl oxazolone of the formula

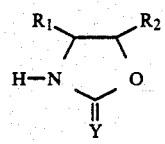

wherein Y is an oxygen or sulfur group; and
  $R_1$ is a hydrogen, or a $(C_1-C_5)$alkyl group, $R_2$ is a phenyl group optionally substituted with one or two members of the group consisting of $(C_1-C_5)$alkyl, $(C_1-C_5)$alkoxy,
  $(C_1-C_5)$alkylthio, $(C_1-C_5)$alkylsulfinyl,
  $(C_1-C_5)$alkylsulfonyl, hydroxy, halogen,
  cyano, carboxy, carb$(C_1-C_5)$alkoxy,
  carbamido, $(C_1-C_5)$alkanoylamino,
  imidazolyl, trifluoromethyl or with a methylenedioxy group.

9. A method of claim 8 wherein Y is an oxygen group.

10. A method of claim 9 wherein $R_1$ is a $(C_1-C_5)$alkyl group.

11. A method of claim 9 wherein $R_2$ is an unsubstituted phenyl group.

12. A method of claim 10 wherein $R_2$ is a substituted phenyl group.

13. A method of claim 10 wherein $R_1$ is a methyl, ethyl or propyl group.

14. A method of claim 13 wherein $R_2$ is a substituted phenyl group.

* * * * *

UNITED STATES PATENT AND TRADEMARK OFFICE
CERTIFICATE OF CORRECTION

PATENT NO. : 4,728,661

DATED : March 1, 1988

INVENTOR(S) : R.L. Schnettler; W.D. Jones; G.P. Claxton

It is certified that error appears in the above-identified patent and that said Letters Patent is hereby corrected as shown below:

At Column 1, Line 51, the patent reads "improved ventricular" and should read --improves ventricular--.

At Column 2, Line 19, after "alkyl" insert --group. The compounds enhance myocardial contractile force and are useful as cardiotonics in the treatment of heart failure.--

At Column 4, Line 13, the patent reads "the reactant preferably" and should read --the reactants preferably--.

At Column 4, Line 64, the patent reads "cadiotonic agents" and should read --cardiotonic agents--.

At Column 5, Line 48, the patent reads "ctive ingredient," and should read --active ingredient,--.

Signed and Sealed this

Tenth Day of October, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,728,661

DATED : March 1, 1988

INVENTOR(S) : R.L. Schnettler, W.D. Jones, G.P. Claxton

It is certified that error appears in the above-identified patent and that said Letters Patent is hereby corrected as shown below:

At column 7, claim 1, line 5, and again at column 8, claim 8, line 5, the structure reads 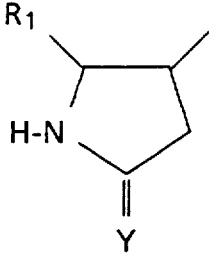 and should read 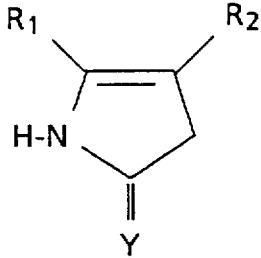

Signed and Sealed this

Twentieth Day of March, 1990

*Attest:*

JEFFREY M. SAMUELS

*Attesting Officer*  *Acting Commissioner of Patents and Trademarks*